United States Patent [19]

Weuthen

[11] Patent Number: 5,545,731
[45] Date of Patent: Aug. 13, 1996

[54] ALKYL AND/OR ALKENYL OLIGOGLYCOSIDE CARBONATES

[75] Inventor: Manfred Weuthen, Solingen, Germany

[73] Assignee: Henkel Kommanditgesellschaft auf Aktien, Duesseldorf, Germany

[21] Appl. No.: 313,178

[22] PCT Filed: Mar. 25, 1993

[86] PCT No.: PCT/EP93/00725

§ 371 Date: Oct. 3, 1994

§ 102(e) Date: Oct. 3, 1994

[87] PCT Pub. No.: WO93/20089

PCT Pub. Date: Oct. 14, 1993

[30] Foreign Application Priority Data

Apr. 2, 1992 [DE] Germany ................. 42 10 913.2

[51] Int. Cl.⁶ ..................... C07H 11/00; C07H 15/04
[52] U.S. Cl. ............... 510/119; 536/116; 536/120; 536/124; 536/115; 424/70.1; 510/276; 510/130; 510/151; 510/235; 510/470
[58] Field of Search ................. 536/4.1, 32, 48, 536/58, 107, 115, 124, 116, 120; 252/89.1; 424/70.1

[56] References Cited

U.S. PATENT DOCUMENTS 5,068,321  11/1991  Buysch et al. ................. 536/32

FOREIGN PATENT DOCUMENTS 0301298  2/1989  European Pat. Off. .
53-023927  3/1978  Japan .

OTHER PUBLICATIONS

Seifen–öle–Fette–Wachse, 117, 124 (1991).
J. Am. Oil Chem. Soc., 36, 553 (1959).
J. Coconut. Stud., 5(1), 51 (1980).
Bull. Acad. Polon, Sci. 9, 103 (1961).
Chim. L'Industr., 18 (1990).

*Primary Examiner*—John W. Rollins
*Attorney, Agent, or Firm*—Wayne C. Jaeschke; John E. Drach; Henry E. Millson, Jr.

[57] ABSTRACT

Alkyl and/or alkenyl oligoglycoside carbonates are obtainable by condensation of alkyl and/or alkenyl oligoglycosides corresponding to formula (I)

$$R^1O-(R^2O)_x-[G]_p \quad (I)$$

in which
$R^1$ is a $C_{1-22}$ alkyl and/or alkenyl radical,
$R^2$ is a $C_{2-4}$ alkylene radical,
x is 0 or a number of 1 to 30,
[G] is a sugar unit containing 5 or 6 carbon atoms and
p is a number of 1 to 10,
with dialkyl carbonates corresponding to formula (II)

$$R^3O-CO-OR^4 \quad (II)$$

in which
$R^3$ and $R^4$ independently of one another represent $C_{1-10}$ alkyl radicals,
in the presence of basic catalysts.

22 Claims, No Drawings

ALKYL AND/OR ALKENYL OLIGOGLYCOSIDE CARBONATES

BACKGROUND OF THE INVENTION

1. Field of the Invention

This invention relates to alkyl and/or alkenyl oligoglycoside carbonates, to a process for their production and to their use for the production of surfactants.

2. Statement of Related Art

For some years now, there has been an increasing trend to produce speciality chemicals for detergents from renewable raw materials, such as for example sugar or starch. One example of this are the alkyl oligoglycosides which, for example, may form an alternative to conventional nonionic surfactants based on fatty alcohol and ethylene oxide. However, the properties of alkyl oligoglycosides are not entirely satisfactory for certain cosmetic applications. Accordingly, esters of alkyl oligoglycosides with carboxylic acids of varying chain length are preferably used instead of alkyl oligoglycosides (Seifen-Öle-Fette-Wachse, 117, 124 (1991)).

However, the production of these alkyl oligoglycoside esters is attended by two problems, namely:

1. the thermal instability of the glycoside base under the esterification conditions with the danger of caramelization and 2. the inadequate solubility of alkyl oligoglycosides in standard solvents.

There has been no shortage of attempts in the past to provide technical solutions to these problems:

For example, Gibbons and Swanson report in J. Am. Oil Chem. Soc., 36, 553 (1959) on their efforts to prepare mono- and diesters from methyl glucoside and fatty acids in the presence of sodium hydroxide, lead oxide and tin soap in xylene as solvent. However, any process for the production of cosmetic products which involves the use of xylene and lead compounds is extremely critical in toxicological terms.

The attempts made by Albano-Garcia and Lorica to repeat the esterification in the presence of acidic and basic catalysts in DMF proved unsatisfactory. The reaction products were inhomogeneous and caramelized. The esterification of coconut oil with methyl glucosides using metallic sodium and potassium soap as catalysts also produced dark-colored products which had to be purified with ethyl acetate and water (J. Coconut. Stud., 5(1), 51 (1980)). A process as complicated as this is also totally unsuitable for working on an industrial scale.

Finally, Zedlinski reports on the direct esterification of fatty acid chlorides with methyl glucoside in Bull. Acad. Polon, Sci. 9, 103 (1961). However, the use of fatty acid chlorides imposes stringent works safety requirements and is undesirable for this reason alone.

Accordingly, the problem addressed by the present invention was to provide new alkyl and/or alkenyl oligoglucoside esters of which the production would not be attended by the disadvantages described above.

DESCRIPTION OF THE INVENTION

The present invention relates to alkyl and/or alkenyl oligoglycoside carbonates obtainable by condensation of alkyl and/or alkenyl oligoglycosides corresponding to formula (I)

$$R^1O-(R^2O)_x-(G)_p \quad (I)$$

in which
- $R^1$ is a $C_{1-22}$ alkyl and/or alkenyl radical,
- $R^2$ is a $C_{2-4}$ alkylene radical,
- x is 0 or a number of 1 to 30,
- (G) is a sugar unit containing 5 or 6 carbon atoms and
- p is a number of 1 to 10, with dialkyl carbonates corresponding to formula (II)

$$R^3O-CO-OR^4 \quad (II)$$

in which
- $R^3$ and $R^4$ independently of one another represent $C_{1-10}$ alkyl radicals, in the presence of basic catalysts.

Accordingly, the new alkyl and/or alkenyl oligoglycoside esters are carbonic acid esters of alkyl and/or alkenyl oligoglycosides. It has surprisingly been found that the condensation of alkyl and/or alkenyl oligoglycosides with dialkyl carbonates takes place substantially completely without any discoloration of the reaction products, irrespective of the chain length of the starting materials. In addition, the problem of inadequate solubility can be overcome by using the dialkyl carbonates in excess and, hence, both as transesterification component and as solvent.

The present invention also relates to a process for the production of alkyl and/or alkenyl oligoglycoside carbonates in which alkyl and/or alkenyl oligoglycosides corresponding to formula (I)

$$R^1O-(R^2O)_x-(G)_p \quad (I)$$

in which
- $R^1$ is a $C_{1-22}$ alkyl and/or alkenyl radical,
- $R^2$ is a $C_{2-4}$ alkylene radical,
- x is 0 or a number of 1 to 30,
- (G) is a sugar unit containing 5 or 6 carbon atoms and
- p is a number of 1 to 10, are condensed with dialkyl carbonates corresponding to formula (II)

$$R^3O-CO-OR^4 \quad (II)$$

in which
- $R^3$ and $R^4$ independently of one another represent $C_{1-10}$ alkyl radicals, in the presence of basic catalysts.

Alkyl and/or alkenyl oligoglycosides, which may be used as starting materials for the production of the alkyl and/or alkenyl oligoglycoside carbonates according to the invention, are known compounds which may be obtained by the relevant methods of preparative organic chemistry. One process for their production is based, for example, on the acid-catalyzed acetalization of glucose with fatty alcohols. European patent application EP-A1-0 301 298 is cited as representative of the extensive literature on this subject.

Preferred alkyl and/or alkenyl oligoglycosides are those derived from aldoses or ketoses and, by virtue of their ready availability, particularly from glucose. Accordingly, preferred alkyl oligoglycosides are alkyl oligoglucosides.

The index p in general formula (I) indicates the degree of oligomerization (DP degree), i.e. the distribution of monoglycosides and oligoglycosides, and is a number of 1 to 10. Whereas p in a given compound must always be an integer and, above all, may assume a value of 1 to 6, the value p for a certain alkyl and/or alkenyl oligoglycoside is an analytically determined calculated value which is generally a broken number. Alkyl oligoglycosides having an average degree of oligomerization p of 1.1 to 3.0 are preferred. Alkyl and/or alkenyl oligoglycosides having a degree of oligomerization of less than 1.7 and, more particularly, between 1.2 and 1.4 are particularly preferred.

The substituent $R^1$ may be derived from saturated and/or unsaturated primary alcohols containing 8 to 22 and preferably 8 to 10 or 12 to 18 carbon atoms. Typical examples are methanol, butanol, caproic alcohol, capric alcohol, 2-ethylhexanol, capryl alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, arachyl alcohol, gadoleyl alcohol, behenyl alcohol and erucyl alcohol and also technical cuts which may contain these alcohols in varying quantities.

In addition, the alkyl and/or alkenyl oligoglycosides may be present in the form of their adducts with 1 to 30 mol ethylene, propylene and/or butylene oxide.

Alkyl and/or alkenyl oligoglycoside carbonates having particularly advantageous performance properties are obtained where alkyl oligoglycosides corresponding to formula (I), in which $R^1$ is a $C_{8-18}$ alkyl radical, x is 0, (G) is a glucose unit and p is a number of 1.3 to 3, are used. $C_{8-10}$ and $C_{12-18}$ alkyl oligoglucosides are particularly preferred.

The dialkyl carbonates are known compounds which may be obtained by relevant methods of organic chemistry. Accordingly, the use of dialkyl carbonates corresponding to formula (II), in which $R^3$ and $R^4$ are methyl and/or ethyl radicals, is of industrial relevance and is therefore preferred in the context of the invention. Information on the production and physical properties of these products can be found, for example, in Chim. L'Industr., 18 (1990).

The choice of the basic catalysts is not critical. However, preferred basic catalysts are alkalis selected from the group consisting of alkali metal and alkaline earth metal oxides, hydroxides, carbonates and $C_{1-4}$ alkylates. Typical examples are sodium hydroxide, sodium carbonate, potassium hydroxide, calcium oxide, sodium methylate and potassium tert. butylate. The basic catalysts may be used in quantities of 0.1 to 5 mol-% and preferably in quantities of 1 to 3 mol-%, based on the alkyl and/or alkenyl oligoglycosides.

The alkyl and/or alkenyl oligoglycosides and the dialkyl carbonates may be used in a molar ratio of 1:1 to 1:15. In the interests of thorough mixing of the reactants, it has proved to be of advantage to use the dialkyl carbonates in excess so that they serve both as esterification component and as solvent. Accordingly, a molar ratio of 1:4 to 1:12 is particularly preferred.

For rapid and complete condensation, it has proved to be sufficient to carry out the reaction at the boiling temperature of the dialkyl carbonate. In one preferred embodiment of the invention, the transesterification is carried out with diethyl carbonate at a temperature of 110° to 120° C.

The reaction of the alkyl and/or alkenyl oligoglycosides with the dialkyl carbonates is a transesterification in which one or more hydroxyl groups of the glucoside react off with one or even both ester groups of the dialkyl carbonate with elimination of alcohol. In accordance with the nature of the condensation reaction, a complex mixture is obtained, although it mainly contains glucoside monoester and, to a lesser extent, diester. On completion of the reaction, the basic crude product may be neutralized and excess dialkyl carbonate and alcohol formed during the condensation reaction may be distilled off in vacuo.

In one particular embodiment of the process according to the invention, part of the alcohol formed is continuously removed from the equilibrium, for example by distillation, during the actual condensation reaction. In this way, the equilibrium is displaced and products distinguished by a high percentage content of diesters are obtained.

Commercial Applications

The alkyl and/or alkenyl oligoglycoside carbonates according to the invention have surface-active properties. They are dermatologically safe and easy to formulate.

Accordingly, the present invention also relates to their use for the production of laundry detergents, dishwashing detergents and cleaning preparations and also haircare and personal hygiene products in which they may be present in quantities of 0.1 to 50% by weight and preferably in quantities of 1 to 25% by weight, based on the preparation or product.

The following Examples are intended to illustrate the invention without limiting it in any way.

EXAMPLES

Example 1

Alkyl oligoglycoside monoethyl carbonate 384 g (1 mol) dodecyl oligoglucoside (DP=1.2), 1180 g (10 mol) diethyl carbonate and 0.02 mol sodium hydroxide were introduced into a 2 liter three-necked flask equipped with a stirrer, reflux condenser and distillation column and heated under reflux for 1 hour with intensive stirring (approx. 120° C.). The reaction mixture was then neutralized with phosphoric acid, after which excess diethyl carbonate and ethanol emanating from the condensation were distilled off in vacuo. The yield amounted to 414 g, corresponding to 91% of the theoretical. The alkyl oligoglucoside monoethyl carbonate was subsequently mixed with 95 g water at 80° C. to form a paste.

Example 2

Alkyl oligoglucoside di(monoethylcarbonate)

The procedure was as in Example 1, except that 61 g (0.8 mol) ethanol was distilled off during the reaction itself. The product was then neutralized and diethyl carbonate and the remaining ethanol formed were distilled off. The yield amounted to 475 g, corresponding to 91% of the theoretical.

What is claimed is:

1. A product comprising a carbonic acid ester of an alkyl or alkenyl oligoglycoside or mixture thereof produced by the process comprising reacting at least one alkyl or alkenyl oligoglycoside of formula I $$R^1O-(R^2O)_x-(G)_p \qquad (I)$$

wherein $R^1$ is a $C_{1-22}$ alkyl or alkenyl radical, $R^2$ is a $C_{2-4}$ alkylene radical, x is 0 or a number from 1 to 30, (G) is a sugar unit containing 5 or 6 carbon atoms and p is a number of 1 to 10; with at least one dialkyl carbonate of the formula (II)

$$R^3O-CO-OR^4 \qquad (II)$$

wherein each of $R^3$ and $R^4$ is independently a $C_{1-10}$ alkyl radical, in the presence of from about 0.1 to about 5 mol percent, based on said oligoglycoside, of at least one basic catalyst, wherein the molar ratio of said oligoglycoside to said dialkyl carbonate is from about 1:1 to about 1:15.

2. The product of claim 1 wherein $R^1$ is a $C_{8-18}$ alkyl radical, x is 0, (G) is a glucose unit and p is a number of 1.3 to 3.

3. The product of claim 1 wherein each of $R^3$ and $R^4$ is independently a methyl or an ethyl radical.

4. The product of claim 1 wherein said basic catalyst is selected from the group consisting of an alkali metal oxide, an alkaline earth metal oxide, alkali metal hydroxide, an alkaline earth metal hydroxide, an alkali metal carbonate, an alkaline earth metal carbonate, a $C_{1-4}$ alkylate, and a combination thereof.

5. The product of claim 1 wherein said reaction is carried out at the boiling temperature of the dialkyl carbonate.

6. The product of claim 1 wherein the alcohol formed as a product of the reaction is continuously removed as it is formed.

7. The product of claim 1 wherein said molar ratio is from about 1:4 to about 1:12.

8. The product of claim 1 wherein the mole percent of basic catalyst is from about 1 to about 3 mol percent.

9. The product of claim 7 wherein the mole percent of basic catalyst is from about 1 to about 3 mol percent.

10. The product of claim 1 wherein said process is carried out at a temperature in the range of from about 110° to about 120° C.

11. In a laundry detergent, dishwashing detergent, cleaning preparation, hair care product, or personal hygiene product, the improvement wherein from about 0.1 to about 50% by weight of the product of claim 1 is present therein.

12. In a laundry detergent, dishwashing detergent, cleaning preparation, hair care product, or personal hygiene product, the improvement wherein from about 1 to about 25% by weight of the product of claim 1 is present therein.

13. A process for making an alkyl or alkenyl oligoglycoside carbonate or mixture thereof comprising reacting at least one alkyl or alkenyl oligoglycoside of formula I

$$R^1O-(R^2O)_x-(G)_p \qquad (I)$$

wherein $R^1$ is a $C_{1-22}$ alkyl or alkenyl radical, $R^2$ is a $C_{2-4}$ alkylene radical, x is 0 or a number from 1 to 30, (G) is a sugar unit containing 5 or 6 carbon atoms and p is a number of 1 to 10; with at least one dialkyl carbonate of the formula (II)

$$R^3O-CO-OR^4 \qquad (II)$$

wherein each of $R^3$ and $R^4$ is independently a $C_{1-10}$ alkyl radical, in the presence of from about 0.1 to about 5 mol percent, based on said oligoglycoside, of at least one basic catalyst, wherein the molar ratio of said oligoglycoside to said dialkyl carbonate is from about 1:1 to about 1:15.

14. The process of claim 13 wherein $R^1$ is a $C_{8-18}$ alkyl radical, x is 0, (G) is a glucose unit and p is a number of 1.3 to 3.

15. The process of claim 13 wherein each of $R^3$ and $R^4$ is independently a methyl or an ethyl radical.

16. The process of claim 13 wherein said basic catalyst is selected from the group consisting of an alkali metal oxide, an alkaline earth metal oxide, alkali metal hydroxide, an alkaline earth metal hydroxide, an alkali metal carbonate, an alkaline earth metal carbonate, a $C_{1-4}$ alkylate, and a combination thereof.

17. The process of claim 13 wherein said reaction is carried out at the boiling temperature of the dialkyl carbonate.

18. The process of claim 13 wherein the alcohol formed as a product of the reaction is continuously removed as it is formed.

19. The process of claim 13 wherein said molar ratio is from about 1:4 to about 1:12.

20. The process of claim 13 wherein the mole percent of basic catalyst is from about 1 to about 3 mol percent.

21. The process of claim 19 wherein the mole percent of basic catalyst is from about 1 about 3 mol percent.

22. The process of claim 13 wherein said process is carried out at a temperature in the range of from about 110° to about 120° C.

* * * * *